United States Patent [19]

Sirrenberg et al.

[11] 4,041,177

[45] Aug. 9, 1977

[54] 4-NITRO-4'-[N-(N'-BENZOYL)-UREIDO]-DIPHENYL ETHERS

[75] Inventors: Wilhelm Sirrenberg, Sprockhoevel; Jürgen Schramm, Dormagen; Erich Klauke, Odenthal; Ingeborg Hammann, Cologne; Wilhelm Stendel, Wuppertal, all of Germany

[73] Assignee: Bayer Aktiengesellschaft, Leverkusen, Germany

[21] Appl. No.: 651,986

[22] Filed: Jan. 23, 1976

[30] Foreign Application Priority Data

Feb. 6, 1975 Germany .............................. 2504983

[51] Int. Cl.² ...................... C07C 127/22; A61K 31/17
[52] U.S. Cl. .................................. 424/322; 260/553 C; 260/553 E; 260/453 AR; 260/578
[58] Field of Search ................. 260/553 C, 553 E; 424/322

[56] References Cited

U.S. PATENT DOCUMENTS

| | | | |
|---|---|---|---|
| 2,649,476 | 8/1953 | Martin | 260/553 CX |
| 2,722,544 | 11/1955 | Martin | 260/553 C X |
| 3,060,235 | 10/1962 | Martin et al. | 260/553 A |
| 3,230,141 | 1/1966 | Frick et al. | 260/553 C X |
| 3,261,865 | 7/1966 | Speziale et al. | 260/553 E |
| 3,284,433 | 11/1966 | Becker et al. | 260/553 C X |
| 3,450,747 | 6/1969 | Smith et al. | 424/244 X |
| 3,748,356 | 7/1973 | Welling et al. | 260/553 C X |
| 3,798,276 | 3/1974 | Bayer et al. | 260/553 A X |
| 3,992,553 | 11/1976 | Sirrenberg et al. | 260/553 A X |
| 4,005,223 | 1/1977 | Sirrenberg et al. | 260/553 A X |

Primary Examiner—Daniel E. Wyman
Assistant Examiner—Thomas A. Waltz
Attorney, Agent, or Firm—Burgess, Dinklage & Sprung

[57] ABSTRACT

4-Nitro-4'-[N-(N'-benzoyl)-ureido]-diphenyl ethers of the general formula

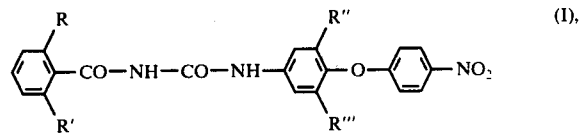

in which
R is chlorine, fluorine or methyl,
R' is hydrogen, chlorine or fluorine, and
R" and R''' are identical and are each hydrogen or chlorine, but if R is chlorine and R' is hydrogen, R" and R''' can only be hydrogen.

which possess insecticidal properties.

13 Claims, No Drawings

4-NITRO-4'-[N-(N'-BENZOYL)-UREIDO]-DIPHENYL ETHERS

The present invention relates to and has for its objects the provision of particular new 4-nitro-4'-[N-(N'-benzoyl)-ureido]-diphenyl ethers, which possess insecticidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It has been disclosed in German Published Specification DOS 2,123,236 that certain benzoylureas, such as, for example, N-(2,6-dichlorobenzoyl)-N'-(4-chlorophenyl (Compound A) and 3,4-dichlorophenyl)-urea (Compound B) possess insecticidal properties.

The present invention provides the benzoylureidonitro-diphenyl ethers of the general formula

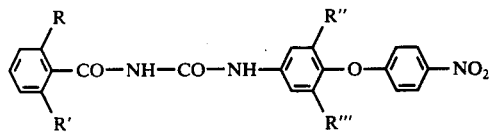 (I), in which
R is chlorine, fluorine or methyl,
R' is hydrogen, chlorine or fluorine, and
R" and R'" are identical and are each hydrogen or chlorine, but if R is chlorine and R' is hydrogen, R" and R'" can only be hydrogen.

A preferred sub-group of compounds is that wherein R is fluorine or methyl. Another preferred sub-group is that in which R is Cl and R' is chlorine or fluorine. In both of these sub-groups R" and R'" are still identical but can be either hydrogen or chlorine.

The present invention also provides a process for the preparation of a benzoylureido-nitro-diphenyl ether of the formula (I), in which a. a phenoxyaniline of the general formula

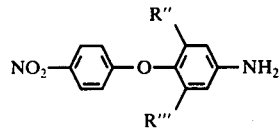 (II), in which
R" and R'" have the above-mentioned meanings,
is reacted with a benzoylisocyanate of the general formula

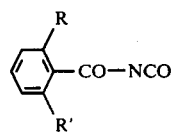 (III), in which
R and R' have the above-mentioned meanings,
if appropriate in the presence of a solvent, or b. a 4-isocyanato-diphenyl ether of the general formula

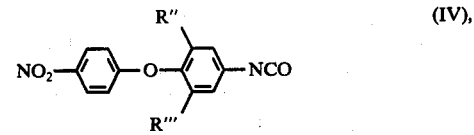 (IV), in which
R" and R'" have the above-mentioned meanings,
is reacted with a benzamide of the general formula

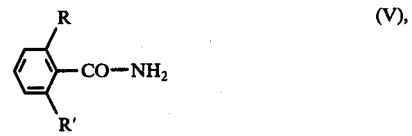 (V), in which
R and R' have the above-mentioned meanings,
if appropriate in the presence of a solvent.

If, using process variant (a), 4-(4'-nitro-phenoxy)aniline and 2,6-difluorobenzoylisocyanate are employed as starting materials and, using process variant (b), 3,5-dichloro-4-(4'-nitro-phenoxy)-phenylisocyanate and 2,6-dichlorobenzamide are employed as starting materials, the courses of the reactions can be represented by the following equations:

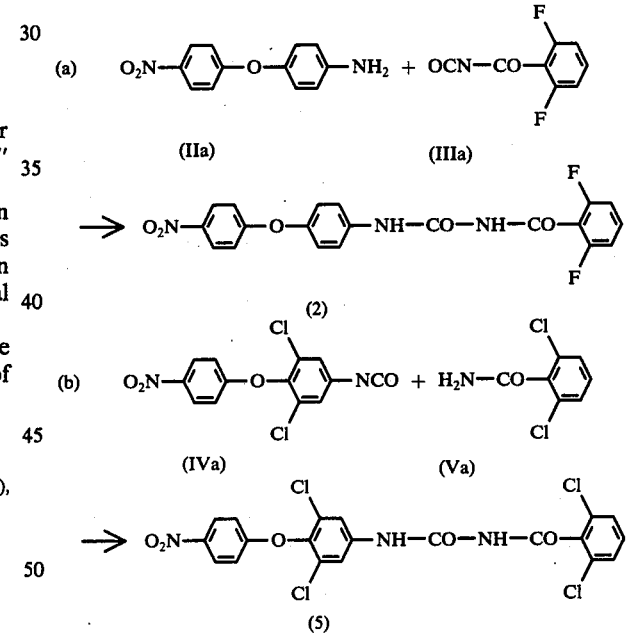

The benzoylisocyanates of the general formula (III) to be used as starting materials are known from the literature and can be prepared according to generally customary processes [see A. J. Speziale et al., J. Org. Chem. 30 (12), pages 4 306–4 307 (1965)]. The benzamides of the general formula (V) are known from the literature and can be prepared according to known methods (see Beilsteins Handbuch der Organischen Chemie (Beilstein's Handbook of Organic Chemistry), volume 9, page 336). The phenoxyanilines of the general formula (II) can be prepared according to generally customary processes, for example from alkali metal aminophenolates and aromatic nitrohalogen compounds in a solvent, for example dimethylsulfoxide (see Jürgen Schramm et al., Justus Liebigs Annalen der Chemie 1970, 740, 169–179). The amino group can be converted to the isocyanate group in accordance with generally customary processes, for example by reaction with phosgene, whereby the 4-isocyanatodiphenyl ethers of the general formula (IV) are obtained.

The following may be mentioned as examples of phenoxyanilines (II) and 4-isocyanato-diphenyl ethers (IV) to be reacted in accordance with the process: 4-(4'-nitrophenoxy)-aniline and 3,5-dichloro-4-(4'-nitrophenoxy)-aniline, and 2,6-dichloro-4-isocyanato-4'-nitro-diphenyl ether and 4-isocyanato-4'-nitro-diphenyl ether.

The process variants (a) and (b) for the preparation of the compounds according to the invention are preferably carried out in the presence of suitable solvents and diluents. Practically all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane ketones, for example acetone, methyl ethyl ketone, methyl isopropyl ketone and methyl isobutyl ketone; and nitriles, such as acetonitrile and benzonitrile.

The reaction temperature can be varied within a fairly wide range. In general the reaction is carried out at between 0° and 120° C, preferably at from 70° to 85° C.

The reaction is in general allowed to take place under normal pressure.

To carry out the process, the reactants are preferably employed in equimolar amounts. An excess of one or the other reactant produces no significant advantages.

The 4-isocyanato-nitro-diphenyl ethers (IV) to be employed in process variant (b) above can be employed as such or, without intermediate isolation, in the form of their reaction mixture which is obtained in the reaction with amine and phosgene. This reaction mixture, in one of the above-mentioned solvents, is treated with the appropriate benzamides. The reaction is carried out under the desired conditions and the product which separates out is isolated in the usual manner by filtration, washing and, if appropriate, recrystallization.

The compounds are obtained in a crystalline form of sharp melting point.

As already mentioned, the benzoylureido-nitro-diphenyl ethers according to the invention are distinguished by an excellent insecticidal activity. They are not only active against plant pests but also, in the veterinary medicine field, against animal parasites (ectoparasites), such as parasitic fly larvae. They possess favorable values for toxicity to warm-blooded animals and are well tolerated by plants.

For this reason, the compounds according to the invention can be employed successfully in plant protection against biting and sucking insects. They can furthermore be employed in the veterinary field as pest control agents against animal parasites.

The active compounds according to the invention can be used for combating all or individual stages of development, including the pre-embryonic, normally sensitive and resistant stages of development, of insects, where these are known as pests in agriculture, in forestry, in the protection of stored products and materials, and in hygiene.

The economically important insect pests in agriculture and forestry, as well as pests of stored products, pests destructive of materials and pests harmful to health include: from the order of the Thysanura, for example, *Lepisma saccharina*; from the order of the Collembola, for example, *Onychiurus armatus*; from the order of the Orthoptera, for example *Blatta orientalis, Periplaneta americana, Leucophaea maderae, Blattella germanica, Acheta domesticus, Gryllotalpha* spec., *Locusta migratoria migratorioides, Melanoplus differentialis* and *Schistocerca gregaria*; from the order of the Dermaptera, for example, *Forficula auricularia*; from the order of the Isoptera, for example, *Reticulitermes* spec.; from the order of the Anoplura, for example, *Phylloxera vastatrix, Pemphigus* spec. and *Pediculus humanus corporis*; from the order of the Thysanoptera, for example, *Hercinothrips femoralis* and *Thrips tabaci*; from the order of the Heteroptera, for example, *Eurygaster* spec., *Dysdercus intermedius, Piesma quadrata, Cimex lectularius, Rhodnius prolixus* and *Triatoma* spec.; from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus cerasi, Myzus persicae, Phorodon humuli, Rhopalosiphum padi, Empoasca* spec., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spec. and *Psylla* spec.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spec., *Bucculatrix thurberiella, Phyllocnistis citrella, Agrotis* spec., *Euxoa* spec., *Feltia* spec., *Earias insulana, Heliothis* spec., *Laphygma exigua, Mamestra brassicae, Panolis flammea, Prodenia litura, Spodoptera* spec., *Trichoplusia ni, Carpocapsa pomonella, Pieris* spec., *Chilo* spec., *Pyrausta nubilalis, Ephestia kühniella, Galleria mellonella, Cacoecia podana, Capua reticulana, Choristoneura fumiferana, Clysia ambiguella, Homona magnanima* and *Tortrix viridana*; from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spec., *Psylliodes chrysocephala, Epilachna varivestis, Atomaria* spec., *Oryzaephilus surinamensis, Anthonomus* spec, *Sitophilus* spec., *Otiorrhynchus sulcatus, Cosmopolites sordidus, Ceuthorrhynchus assimilis, Hypera postica, Dermestes* spec., *Trogoderma* spec., *Anthrenus* spec., *Attagenus* spec., *Lyctus* spec., *Meligethes aeneus, Ptinus* spec., *Niptus hololeucus, Gibbium psylloides, Tribolium* spec., *Tenebrio molitor, Agriotes* spec., *Conoderus* spec., *Melolontha melolontha, Amphimallus solstitialis* and *Costelytra zealandica*; from the order of the Hymenoptera, for example, *Diprion* spec., *Hoplocampa* spec., *Lasium* spec., *Monomorium pharaonis* and *Vespa* spec.; from the order of the Diptera, for example, *aëdes* spec., *Anopheles* spec., *Culex* spec., *Drosophila melanogaster, Musca domestica, Fannia* spec., *Stomoxys calcitrans, Hypoderma* spec., *Bibio hortulanus, Oscinella frit, Phorbia* spec., *Pegomyia hyoscyami, Calliphora erythrocephala, Lucilia* spec., *Chrysomyia* spec., *Ceratitis capitata, Dacus oleae* and *Tipula paludosa*; and from the order of the Siphonaptera, for example, *Xenopsylla cheopis*.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.) halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.) amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.) and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, or acaricides, rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these are generally contemplate carrier composition mixtures in which the active compound is present in an amount substantially between 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 h/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present invention contemplates methods of selectively killing, combating or controlling pests, e.g. insects, which comprises applying to at least one of correspondingly (a) such insects, and (b) the corresponding habitat thereof, i.e. the locus to be protected, a correspondingly combative or toxic amount, i.e. an insecticidally effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

Table 1
(Insects which damage plants)
Plutella test

| Active compound | | Active compound concentration in % | Degree of destruction in % after 8 days |
|---|---|---|---|
| [Structure: 2,6-dichlorobenzoyl with Cl] –CO–NH–CO–NH– [phenyl]–Cl (known) | (A) | 0.1<br>0.01 | 65<br>0 |
| [Structure: 2,6-dichlorobenzoyl] –CO–NH–CO–NH– [2,6-dichlorophenyl] (known) | (B) | 0.1<br>0.01<br>0.001 | 100<br>100<br>15 |
| [Structure: 2-CH₃-benzoyl] –CO–NH–CO–NH– [2,6-dichloro-4-(4-nitrophenoxy)phenyl] | (4) | 0.1<br>0.01<br>0.001 | 100<br>100<br>100 |
| [Structure: 2-F-benzoyl] –CO–NH–CO–NH– [2,6-dichloro-4-(4-nitrophenoxy)phenyl] | (3) | 0.1<br>0.01<br>0.001 | 100<br>100<br>100 |
| [Structure: 2,6-difluorobenzoyl] –CO–NH–CO–NH– [4-(4-nitrophenoxy)phenyl] | (2) | 0.1<br>0.01<br>0.001 | 100<br>100<br>100 |
| [Structure: 2,6-difluorobenzoyl] –CO–NH–CO–NH– [2,6-dichloro-4-(4-nitrophenoxy)phenyl] | (1) | 0.1<br>0.01<br>0.001 | 100<br>100<br>100 |
| [Structure: 2-CH₃-benzoyl] –CO–NH–CO–NH– [4-(4-nitrophenoxy)phenyl] | (7) | 0.1<br>0.01<br>0.001 | 100<br>100<br>100 |

EXAMPLE 2

Phaedon larvae test

Solvent: 3 parts by weight of dimethylformamide
Emulsifier: 1 part by weight of alkylaryl polyglycol ether After the specified periods of time, the degree of destruction was determined in %: 100% means that all of the beetle larvae had been killed whereas 0% means that none of the beetle larvae had been killed.

The active compounds, the concentrations of the active compounds, the evaluation times and the results can be seen from the following table:

Table 2
(Insects which damage plants)
Phaedon larvae test

| Active compounds | | Active compound concentration in % | Degree of destruction in % after 3 days |
|---|---|---|---|
| [Structure: 2,6-dichlorobenzoyl] –CO–NH–CO–NH– [phenyl]–Cl (known) | (A) | 0.1<br>0.01<br>0.001 | 100<br>55<br>0 |
| [Structure: 2,6-dichlorobenzoyl] –CO–NH–CO–NH– [2,6-dichlorophenyl] | (B) | 0.1<br>0.01<br>0.001 | 100<br>15<br>0 |

Table 2-continued

(Insects which damage plants)
Phaedon larvae test

| Active compounds | | Active compound concentration in % | Degree of destruction in % after 3 days |
|---|---|---|---|
| (known) 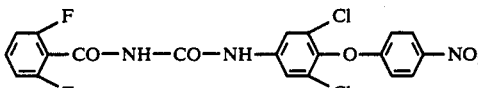 | (1) | 0.1<br>0.01<br>0.001 | 100<br>100<br>80 |

EXAMPLE 3

Test with parasitic fly larvae

Solvent: 35 parts by weight of ethylene polyglycol monomethyl ether 35 parts by weight of nonylphenol polyglycol ether To produce a suitable preparation of active compound, 30 parts by weight of the active substance in question were mixed with the stated amount of solvent which contained in the above-mentioned proportion of emulsifier and the concentrate thus obtained was diluted with water to the desired concentration.

About 20 fly larvae (*Lucilia cuprina*) were introduced into a test tube which contained approx. 2 cm³ of horse muscle. 0.5 ml of the preparation of active compound was applied to this horse meat. After 24 hours, the degree of destruction in % was determined. 100% means that all larvae had been killed and 0% means that no larvae had been killed.

The active compounds investigated, the concentrations of the active compounds used and the results obtained can be seen from the table which follows:

A solution of 3.7 g (0.02 mole) of 2,6-difluorobenzoylisocyanate in 20 ml of toluene was added dropwise, at 80° C, to 6 g (0.02 mole) of 3,5-dichloro-4-(4'-nitrophenoxy)-aniline in 100 ml of toluene. The batch was stirred for 1 hour at 80° C. After cooling, the product which had precipitated was filtered off and washed, first with toluene and then with petroleum ether. After drying, 8 g (83% of theory) of analytically pure 4-nitro-2',6'-dichloro-4'-[N-(N'-2,6-difluorobenzoyl)-ureido]-diphenyl ether of melting point 226° were obtained.

EXAMPLE 5

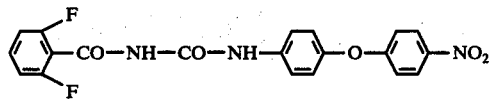 (2)

A solution of 9.2 g (0.05 mole) of 2,6-difluorobenzoylisocyanate in 20 ml of toluene was added dropwise, at 80° C, to a solution of 11.5 g (0.05 mole) of 4-(4'-nitrophenoxy)aniline in 100 ml of toluene and 30 ml of acetonitrile. The batch was stirred for 1 hour at 80° C. The

Table 3

(Test with parasitic fly larvae/Lucilia cuprina/resistant)

| Active compound | | Active compound concentration in ppm | Degree of destruction in % |
|---|---|---|---|
| 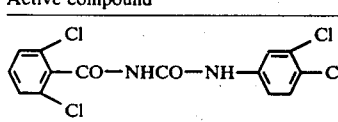 | (B) | 1000 | 0 |
| (known) 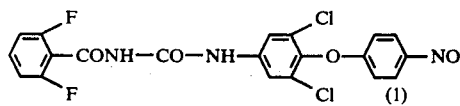 | (1) | 1000<br>100 | 100<br>100 |
| 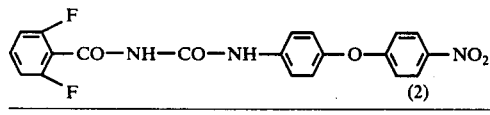 | (2) | 1000<br>300 | 100<br>100 |

The process according to this invention is illustrated by the following preparative Examples.

EXAMPLE 4

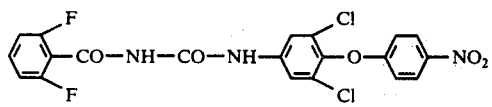 (1)

substance which separated out was filtered off after cooling the reaction mixture to 20° C, and was washed with toluene and petroleum ether. After drying, 18 g (87% of theory) of 4-nitro-4'-[N-(N'-2,6-difluorobenzoyl)-ureido]-diphenyl ether of melting point 240° C were obtained.

The following compounds were prepared by methods analogous methods:

Table 4

| Compound | Formula | Yield (% of theory) | Physical data (melting point °C) |
|---|---|---|---|
| 3 | 2-F-C6H4-CO-NH-CO-NH-(2,6-diCl-C6H2)-O-C6H4-NO2 | 88 | 207 |
| 4 | 2-CH3-C6H4-CO-NH-CO-NH-(2,6-diCl-C6H2)-O-C6H4-NO2 | 76 | 201 |
| 5 | 2,6-diCl-C6H3-CO-NH-CO-NH-(2,6-diCl-C6H2)-O-C6H4-NO2 | 84 | 239 |
| 6 | 2-Cl-C6H4-CO-NH-CO-NH-C6H4-O-C6H4-NO2 | 75 | 215 |
| 7 | 2-CH3-C6H4-CO-NH-CO-NH-C6H4-O-C6H4-NO2 | 61 | 193 |

Other compounds which can be similarly prepared include:

Table 5

(8) 2,6-diCl-C6H3-CO-NH-CO-NH-C6H4-O-C6H4-NO2

(9) 2-Cl-6-F-C6H3-CO-NH-CO-NH-C6H4-O-C6H4-NO2

(10) 2-Cl-6-F-C6H3-CO-NH-CO-NH-(2,6-diCl-C6H2)-O-C6H4-NO2

(11) 2-F-C6H4-CO-NH-CO-NH-C6H4-O-C6H4-NO2

(12) 2-CH3-6-Cl-C6H3-CO-NH-CO-NH-C6H4-O-C6H4-NO2

(13) 2-CH3-6-Cl-C6H3-CO-NH-CO-NH-(2,6-diCl-C6H2)-O-C6H4-NO2

(14) and 2-CH3-6-F-C6H3-CO-NH-CO-NH-C6H4-O-C6H4-NO2

(15) 2-CH3-6-F-C6H3-CO-NH-CO-NH-(2,6-diCl-C6H2)-O-C6H4-NO2

It will be appreciated that the instant specification and examples are set forth by way of illustration and not limitation, and that various modifications and changes may be made without departing from the spirit and scope of the present invention.

What is claimed is:

1. A 4-nitro-4'-[N-(N'-benzoyl)-ureido]-diphenyl ether of the formula

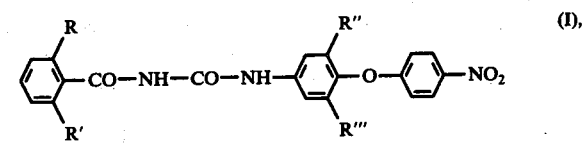

in which
R is chlorine, fluorine, or methyl,
R' is hydrogen, chlorine or fluorine, and
R" and R'" are identical and are each hydrogen or chlorine, but if R is chlorine and R' is hydrogen, R" and R'" can only be hydrogen.

2. The compound according to claim 1, wherein such compound is 4-nitro-4'-[N-(N'-2-chlorobenzoyl)-ureido]-diphenyl ether of the formula

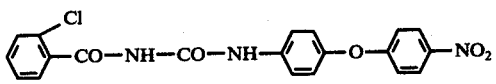

3. A compound according to claim 1, wherein R is fluorine or methyl.

4. The compound according to claim 3, wherein such compound is 4-nitro-2',6'-dichloro-4'-[N-(N'-2,6-difluorobenzoyl)-ureido]-diphenyl ether of the formula

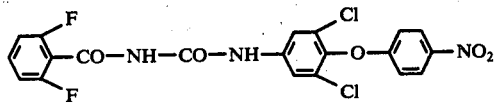

5. The compound according to claim 3, wherein such compound is 4-nitro-4'-[N-(N'-2,6-difluorobenzoyl)-ureido]-diphenyl ether of the formula

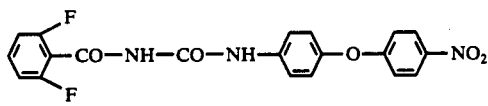

6. The compound according to claim 3, wherein such compound is 4-nitro-2',6'-dichloro-4'-[N-(N'-2-fluorobenzoyl)-ureido]-diphenyl ether of the formula

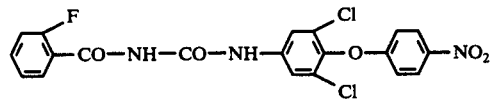

7. The compound according to claim 3, wherein such compound is 4-nitro-2',6'-dichloro-4'-[N-(N'-2-methylbenzoyl)-ureido]-diphenyl ether of the formula

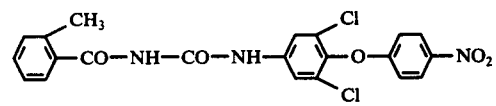

8. The compound according to claim 3, wherein such compound is 4-nitro-4'-[N-(N'-2-methylbenzoyl)-ureido]-diphenyl ether of the formula

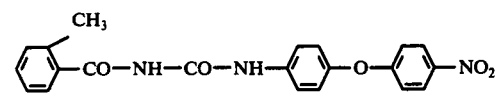

9. A compound according to claim 1, wherein R is chlorine and R' is chlorine or fluorine.

10. The compound according to claim 9, wherein such compound is 4-nitro-2',6'-dichloro-4'-[N-(N'-2,6-dichlorobenzoyl)-ureido]-diphenyl ether of the formula

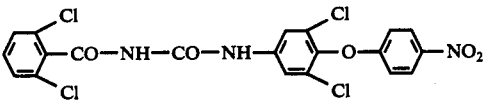

11. An insecticidal composition containing as active ingredient an insecticidally effective amount of a compound according to claim 1 in admixture with a diluent.

12. A method of combating insects which comprises applying to the insects or an insect habitat an insecticidally effective amount of a compound according to claim 1.

13. The method according to claim 12, in which said compound is
4-nitro-4'-[N-(N'-2-chlorobenzoyl)-ureido]-diphenyl ether,
4-nitro-2',6'-dichloro-4'-[N-(N'-2,6-difluorobenzoyl)-ureido]-diphenyl ether,
4-nitro-4'-[N-(N'-2,6-difluorobenzoyl)-ureido]-diphenyl ether,
4-nitro-2'-6'-dichloro-4'-[N-(N'-2-fluorobenzoyl)-ureido]-diphenyl ether,
4-nitro-2',-6'-dichloro-4'-[N-(N'-2-methylbenzoyl)ureido]-diphenyl ether,
4-nitro-4'-[N-(N'-2-methylbenzoyl)-ureido]-diphenyl ether or
4-nitro-2',6'-dichloro-4'-[N'-2,6-dichlorobenzoyl)-ureido]-diphenyl ether.

* * * * *